United States Patent [19]
Shemwell et al.

[11] Patent Number: 6,026,312
[45] Date of Patent: Feb. 15, 2000

[54] METHOD AND APPARATUS FOR DIODE LASER PULSE OXIMETRY USING FIBER OPTICAL CABLES

[75] Inventors: David M. Shemwell, Seattle, Wash.; George R. Ryan, Level Green, Pa.

[73] Assignee: Respironics, Inc., Pittsburgh, Pa.

[21] Appl. No.: 08/876,181

[22] Filed: Jun. 23, 1997

Related U.S. Application Data

[63] Continuation of application No. 08/505,035, Jul. 21, 1995, abandoned.

[51] Int. Cl.[7] .................................................. A61B 5/00
[52] U.S. Cl. ............................................ 600/310; 600/322
[58] Field of Search .......................... 600/310, 314–317, 600/322–324, 326, 328, 334, 473, 476

[56] References Cited

U.S. PATENT DOCUMENTS

| | | |
|---|---|---|
| 3,799,672 | 3/1974 | Vurek . |
| 3,847,483 | 11/1974 | Shaw et al. . |
| 3,951,514 | 4/1976 | Medina, Jr. . |
| 3,998,550 | 12/1976 | Konishi et al. . |
| 4,111,552 | 9/1978 | Auracher et al. ........................ 385/74 |
| 4,167,331 | 9/1979 | Nielsen . |
| 4,265,511 | 5/1981 | Nicia et al. ................................ 385/74 |
| 4,342,907 | 8/1982 | Macedo et al. . |
| 4,407,290 | 10/1983 | Wilber . |
| 4,597,631 | 7/1986 | Flores . |
| 4,621,642 | 11/1986 | New, Jr. et al. . |
| 4,621,643 | 11/1986 | New, Jr. et al. ........................ 128/633 |
| 4,666,045 | 5/1987 | Gillespie et al. . |
| 4,753,530 | 6/1988 | Knight et al. . |
| 4,763,976 | 8/1988 | Nolan et al. . |
| 4,773,442 | 9/1988 | Isaacson et al. . |
| 4,805,623 | 2/1989 | Jöbsis ....................................... 356/41 |
| 4,819,752 | 4/1989 | Zelin . |
| 4,824,242 | 4/1989 | Frick et al. . |
| 4,848,901 | 7/1989 | Hood, Jr. . |
| 4,882,492 | 11/1989 | Schlager ................................. 128/633 |
| 4,883,353 | 11/1989 | Hausman et al. . |
| 4,890,619 | 1/1990 | Hatschek . |

(List continued on next page.)

FOREIGN PATENT DOCUMENTS

| | | |
|---|---|---|
| 95306621 | 3/1996 | European Pat. Off. . |
| 745348A1 | 12/1996 | European Pat. Off. . |

OTHER PUBLICATIONS

Technical Staff of CSELT, *Optical Fibre Communication*, 1980, pp. 13–17.

*Primary Examiner*—Linda C. M. Dvorak
*Assistant Examiner*—Bryan K. Yarnell
*Attorney, Agent, or Firm*—Reed Smith Shaw & McClay LLP

[57] ABSTRACT

A method and apparatus for transferring two frequencies of electromagnetic energy to and from a portion of a living body for the purpose of blood oxygen saturation measurements. The two frequencies of electromagnetic energy are transferred to the portion of the living body through a single optical fiber cable (which could be a bundle) to a coupler and then through a short section of optical cable to an optical element adjacent to the portion of the living body. After the two frequencies of electromagnetic energy are transmitted through the portion of the living body they are received by another optical element and transported away from the portion of the living body to a coupler through a short section of optical cable where they may be converted to electrical signals. Alternatively, the two frequencies of electromagnetic energy are carried away from the coupler. The signals from the coupler (whether they are electromagnetic signals or electrical signals) are directed to a measurement instrument, which through an adapter may be a conventional measurement instrument known in the prior art or a measurement instrument specifically designed for use with the signals produced at the coupler.

4 Claims, 1 Drawing Sheet

U.S. PATENT DOCUMENTS

| | | |
|---|---|---|
| 4,908,676 | 3/1990 | Dedell et al. . |
| 4,935,267 | 6/1990 | Plummer et al. . |
| 4,948,248 | 8/1990 | Lehman ................................. 128/633 |
| 5,039,491 | 8/1991 | Saaski et al. . |
| 5,090,410 | 2/1992 | Saper et al. . |
| 5,103,829 | 4/1992 | Suzuki et al. ........................... 128/633 |
| 5,109,452 | 4/1992 | Selvin et al. . |
| 5,127,071 | 6/1992 | Go . |
| 5,209,230 | 5/1993 | Swedlow et al. . |
| 5,237,442 | 8/1993 | Khoe et al. . |
| 5,249,576 | 10/1993 | Goldberger et al. . |
| 5,262,644 | 11/1993 | Maguire . |
| 5,263,075 | 11/1993 | McGann . |
| 5,279,295 | 1/1994 | Martens et al. . |
| 5,285,783 | 2/1994 | Secker . |
| 5,285,784 | 2/1994 | Seeker . |
| 5,309,537 | 5/1994 | Chun et al. . |
| 5,337,744 | 8/1994 | Branigan . |
| 5,339,810 | 8/1994 | Ivers et al. ............................... 600/340 |
| 5,349,951 | 9/1994 | Ito et al. ................................. 128/633 |
| 5,353,791 | 10/1994 | Tamura et al. . |
| 5,355,880 | 10/1994 | Thomas et al. . |
| 5,355,882 | 10/1994 | Ukawa et al. . |
| 5,357,953 | 10/1994 | Merrick et al. ......................... 128/633 |
| 5,385,143 | 1/1995 | Aoyagi . |
| 5,411,023 | 5/1995 | Morris et al. . |
| 5,413,100 | 5/1995 | Barthelemy et al. . |
| 5,435,309 | 7/1995 | Thomas et al. ......................... 128/633 |
| 5,494,032 | 2/1996 | Robinson et al. . |

METHOD AND APPARATUS FOR DIODE LASER PULSE OXIMETRY USING FIBER OPTICAL CABLES

This application is a continuation of application Ser. No. 08/505,035, filed on Jul. 21, 1995, now abandoned, the contents of which are hereby incorporated by reference.

TECHNICAL FIELD

The present invention relates to methods and apparatus for exposing a living body to electromagnetic energy, and more particularly, to methods and apparatus for exposing a living body to laser light energy via multifiber optical cables and for receiving the laser light energy via multifiber optical cables after passage through the living body.

BACKGROUND OF THE INVENTION

It is possible to determine the oxygen saturation level in the blood stream of a living being by comparing the absorption of two different wavelengths of light, typically red and infared, after the light has transited a blood saturated portion of the body. In practice on humans, the section of the body illuminated is usually a finger, earlobe, hand, foot or the nose. This task is typically accomplished by using two light emitting diodes, one red and one infrared. The diodes are placed in contact with the skin, and photodiodes record the respective amounts of light from each source that is transmitted.

There are a number of problems associated with this current art method. It is important that the wavelengths of the light be carefully controlled so that the amount of the absorbed portion of the incident light is calibrated, and the data is therefore accurate. In the case of light emitting diodes (LEDs) there is a wide variability in wavelength intrinsic to the mass production process. The actual wavelength of light produced also depends on the applied voltage. It is therefore possible to establish the wavelength of the light produced by an LED for this method by matching the wavelength variability of the individual LED with a specific applied voltage. The specific voltage applied to the LED may be established by using a series of resistors in conjunction with a known constant voltage source. One problem with this approach is that each individual LED must be treated. The LED must be customized by matching it with a specific set of resistors. This process is time consuming and expensive. Typically without this customization this technique requires extensive calibration of the calibration equipment and of the sensor to the equipment. This results in a long term problem of sensor interchangeability from unit to unit and between pieces of competitive equipment.

Another problem associated with current art is that the LED is typically in direct contact with the skin of the patient to be treated. LEDs are typically 20 to 30 percent efficient; therefore 70 to 80 percent of the applied electrical power is dissipated in the form of heat. In some cases this excess heat has been known to burn the patient, particularly when current art sensors are used for infant or neonatal care.

The two LEDs which produce the two wavelengths necessary for the measurement are not co-located in the current art. This means that the pathway of the two different forms of light is different and when the patient moves about, it is possible for the pathways to vary and to vary differently. This contributes to an effect known in the community as "motion artifact." The accuracy of the present method depends on the absorption varying only due to differential absorption in the blood. Therefore, varying pathways can lead to absorption variations which do not depend on the blood and can, accordingly, degrade the blood oxygen measurement. A major problem with the current technology is the resulting false alarms.

The wavelength range of an LED light source, while narrow in wavelength spread compared to an incandescent source, is still very broad. It is therefore difficult for LED-based measurement systems to filter out other lights (such as room lights) which are part of the environment rather than the desired light source. In the current art, room light can degrade the measurement.

Two additional problems with the current art are probe positioning on the finger and skin pigmentation. In almost 100% of the cases where the current art is used, the caregiver must apply the probe and reposition the probe to obtain enough signal to allow the system to calibrate and operate. This method is time-consuming and costly. It is also well-known that the current art does not work well on individuals with highly pigmented skin.

SUMMARY OF THE INVENTION

According to one aspect, the invention is an apparatus for transmitting electromagnetic energy through a portion of a living body. The apparatus comprises first and second sources of electromagnetic energy, a first conduit and a detector. The first source produces electromagnetic energy having a first frequency and the second source produces electromagnetic energy having a second frequency. The first conduit transmits the electromagnetic energies having the first and second frequencies from the first and second sources to the vicinity of the portion of the living body. Light from the first conduit is directed into the body. After transiting the portion of the body the light of both frequencies is then received for analysis. The detector converts the electromagnetic energies to corresponding first and second electrical signals after the transmitted electromagnetic energies have passed through the portion of the living body. The detector may be either a sensor located in the vicinity of the body, or another fiber optic cable (a second conduit). When a second conduit is used the detector may be located remotely from the portion of the body.

In accordance with a second aspect, the invention is a method for transmitting electromagnetic energy through a portion of a living body, the method comprising the steps of: a) providing a source of electromagnetic energy having a first frequency, b) providing a source of electromagnetic energy having a second frequency, c) providing a first conduit to transmit the electromagnetic energies from the sources to the vicinity of the portion of the living body and connecting the first conduit to the sources, d) providing a second conduit to receive the transmitted light, e) providing a detector for analyzing the signal. Portions of the first and second conduits may be detachable, in which case an optical coupler is used at the detached point.

DETAILED DESCRIPTION OF THE PREFERRED EMBODIMENT OF THE INVENTION

Figure 1:
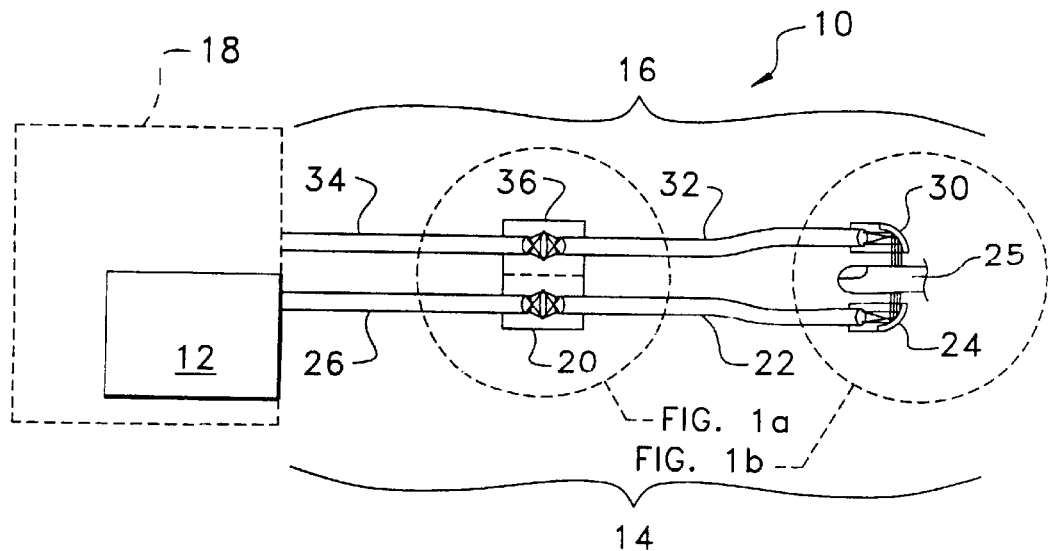
FIG. 1 is a schematic diagram of a preferred embodiment of the apparatus of the invention.

The present invention addresses all of the problems listed above for the current art. FIG. 1 is a schematic diagram of a preferred embodiment of the apparatus of the invention. The apparatus 10 includes a light source 12, a first conduit 14, and a second conduit 16 (which in its totality is the detector portion of the apparatus 10). In the preferred embodiment of the invention, the light source 12 includes a pair of standard (non-customized) diode lasers respectively serving as first and second sources of electromagnetic energies. One electromagnetic energy has a frequency corresponding to red light and the other electromagnetic energy has a frequency corresponding to infrared light. These diode lasers are not in contact with the patient. Instead the diode lasers deliver the light through the first conduit 14, which consists of one or more fiber optical cables. These cables may be composed of either a single fiber or a bundle of fibers. The light from the lasers is introduced to the first conduit 14 by means of a conventional beam splitter, such as a dichroic beam splitter. The dichroic beam splitter allows the laser light from one of the diode lasers to pass along a straight-line path into the first conduit 14 and causes the laser light from the other of the diode lasers to be reflected from another direction (say, 90 degrees from the straight-line path of the light from the first diode laser) into the first conduit 14.

If the cables are of the conventional type, composed of a bundle of optical fibers (typically ranging from several fibers to a thousand fibers), as will be described subsequently, efficient coupling of laser light energy can be accomplished through the use of imaging lenses at the ends of the optical fiber bundle. The lenses should provide a 1:1 imaging of the image presented to the end of the bundle. In the case where two optical fiber bundles are placed end-to-end, the desired 1:1 imaging can be accomplished by indexing (or "clocking") means which cause each of the fibers in one bundle to be substantially aligned with car responding fibers in the other bundle. In addition, the lens can be used to slightly defocus the image it receives from one optical fiber bundle before transmittal to the other optical fiber bundle in order to keep the transfer of laser light energy efficient.

In the preferred embodiment, both diode lasers deliver the light through a single optical fiber cable(which may have many conductors). The frequency of the laser light is tightly controlled during manufacturing so that no additional tuning of the light is required. In addition, unlike the practice with the current art, the laser light source in the inventive system is not discarded after each use. Instead the laser light source 12 resides with a measurement instrument 18. The measurement instrument 18 can be either a unit known in the conventional current art or a special unit designed to interpret electrical signals produced by the second conduit 16.

The technique of fiber delivery that is part of this inventive system, if combined with LEDs instead of lasers, eliminates the requirement for customization used in the current art.

In addition, the inventive method of delivery reduces the "motion artifact" since both wavelengths of light come from the same physical location (the fiber bundle). The reduction of motion artifact reduces, if not totally eliminates, false alarms, thereby increasing the safety of the system. In order to allow the operator the ability to discard the portion of the measurement system which comes into contact with the patient (required due to sterilization concerns), the first conduit 14 of the inventive system uses a coupler 20 and short length 22 of fiber cable in the portion which terminates in an optical element 24 which contacts a portion 25 (such as a finger) of the patient. The first conduit 14 also includes a main fiber cable 26, which is connected to the source 12 (including the lasers) and coupled to the short length 22 of fiber cable using a plastic connector 28 which contains optics designed to efficiently image the light from the main fiber cable 26 into the short length 22 of fiber cable. This short length 22 of fiber cable is inexpensive and keeps the cost of the discarded portion of the system to a minimum (much less than the cost of the current art, where the customized light sources themselves are discarded). The two wavelengths of light come from the same physical location (the short length 22 of fiber cable and the optical element 24). The inventive method of delivery reduces the "motion artifact" since both wavelengths come from the same physical location; i.e., a single optical fiber cable. The invention eliminates the need for equipment calibration and costly software.

Figure 1A:
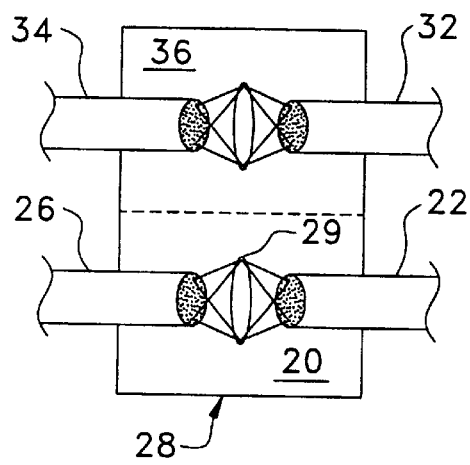
FIG. 1a is a schematic diagram of a preferred embodiment of the fiber optic cable coupler of the invention.

FIG. 1a is a schematic diagram of a preferred embodiment of the fiber optic cable coupler 20 of the invention. The plastic connector 28 includes the fiber optic coupler 20 (and possibly also a fiber optic coupler 36—described subsequently). The preferred embodiment of the fiber optic cable coupler 20 is intended to receive fiber cables 22 and 26 which are multifiber optical cables. The multifiber optical cables allow for inexpensive coupling between the fiber cables 22 and 26 which also features a large signal-gathering area which allows a good signal-to-noise ratio to be maintained.

The multifiber optical cables are indexed relative to the coupler 20 so as to maximize the transfer of light energy from the fiber cable 26 to the fiber cable 22 by aligning the fibers within the fiber cables 22 and 26. The rotational alignment of the fiber cables 22 and 26 is accomplished by the indexing.

The coupler 20 includes a conventional imaging lens 29 which provides 1:1 imaging of the end of the fiber cable 26 onto the end of the fiber cable 22. Although this arrangement will work when the fiber cables 22 and 26 and the lens 29 are spaced so that an exactly focused image of the end of the fiber cable 22 is formed on the end of the fiber cable 26, it can be advantageous to adjust the spacing of these components to provide a slight defocus of the image of the end of the fiber cable 22 on the end of the fiber cable 26. This allows for small misalignments of the components introduced during manufacturing.

The use of remotely mounted lasers allows for the use of extremely bright sources (including remote LEDs) compared to the current art. Laser sources have a very narrow wavelength which allows effective discrimination of the signal from room lights through the use of narrow band optical filters. As shown in FIG. 1, the short length 22 of fiber cable delivers only light to the patient; the excess heat due to the inherent inefficiency of all light sources is dissipated at the other end of the short length 22 of fiber cable from the patient. This arrangement eliminates any chance of burning the patient with waste heat.

The second conduit 16 may have either of two configurations. In one configuration the second conduit 16 includes an optical element 30 and a short length 32 of optical fiber cable, which is attached to a main cable 34 via a coupler 36 (which may be the same as the coupler 20). The main cable 34 is similar to the main fiber cable 26. In this case the preferred embodiment includes the optical element 30 which is a small plastic light collection optic (reflective and/or refractive) bonded onto the patient end of the short length 32 of fiber optic cable. This optic gathers the transmitted light and focuses it into the fiber bundle. After the coupler 36 is the connector which couples the two fibers in the short length 32 of fiber optic cable to the main fiber 34. The main fiber 34 is a length of non-disposable fiber optic cable. In a second preferred configuration, the disposable portion includes a short length 32 of optic fiber cable, conventional photodetectors (such as photodiodes, photomultiplier tubes, CdS sensors, etc., not shown), and a connector (not shown) which couples the short length 32 of optic fiber cable and a receiver electrical connector to carry electrical signals with the main fiber 34.

Figure 1B:
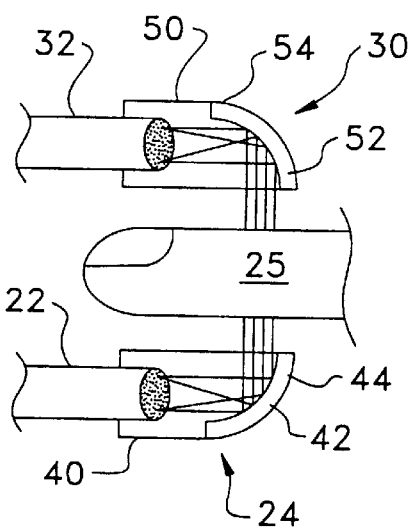
FIG. 1b is a schematic diagram of a preferred embodiment of the optical element of the invention.

FIG. 1b is a schematic diagram of a preferred embodiment of the optical elements 24 and 30 of the invention. Each of the optical elements 24 and 30 are located in close proximity to the portion 25 of the body of the patient. The optical element 24 includes a housing 40 which contains an optical element 42 and means (not shown) for receiving the short length 22 of fiber cable. The optical element 42 receives laser light from the end of the short length 22 of fiber cable and redirects and focuses the laser light into the portion of the body of the patient. The optical element 42 redirects and focuses the laser light by refraction through the body of the optical element 24 (which is preferably made from an inexpensive plastic material), or by reflection from an inexpensive reflective coating 44 on the optical element 24, or by a combination of both.

Similarly, the optical element 30 includes a housing 50 which contains an optical element 52 and means (not shown) for receiving the short length 32 of fiber cable. The optical element 52 receives the laser light that has been transmitted through the portion 25 of the body of the patient and redirects and focuses the laser light onto the end of the short length 32 of fiber cable. The optical element 52 redirects and focuses the laser light by refraction through the body of the optical element 30 (which is also preferably made from an inexpensive plastic material), or by reflection from an inexpensive reflective coating 54 on the optical element 30, or by a combination of both.

The optical element 24 is held in close proximity to the portion 25 of the body of the patient in order to minimize the leakage of light around the portion 25 of the body of the patient, so that the system 10 responds only to laser light which has passed through the portion 25 of the body of the patient.

The methods of redirecting the laser light (as described above) are well-known by those skilled in the art of optical element design. However, in this application, they dramatically improve the efficiency of the measurement and reduce artifacts by limiting the field of view of the sensor to the portion 25 of the body of the patient.

In a particular embodiment the lasers and detectors are matched to an interface circuit. This circuit mimics the behavior of current sensor technologies. In this manner existing pulse oximetry systems may be used in conjunction with this new sensor technology.

The present invention removes the current art requirement of matching or binning of components. This in turn results in a simple software program, eliminating the need for calibration and look-up tables and reduced cost of the disposable portion of the probe. In addition the use of lasers allows for significant enhancement of signal to noise levels, while eliminating the problem of waste heat being dissipated on the patient's skin.

Another advantage the invention provides over current art is the elimination of an extraneous electrical pathway to ground. Due to the inherent nature of the inventive system the antenna effect of the connector cable is eliminated, enhancing the signal-to-noise ratio. Moreover, the natural properties of the plastic cable provide a high degree of insulation and isolation to any stray electrical currents.

In today's hospital environment the two biggest concerns are cost containment and cross contamination of infectious disease. The present invention provides for a true disposable device reduced in cost of manufacturing when compared with ordinary current art disposable sensors. At the same time performance is enhanced compared to the current art.

In addition to the advances in noise reduction and the reduction of motion artifact, the new art reduces the current problem of inaccurate saturation readings due to skin pigmentation. The current art is susceptible to erroneous readings caused by low signal levels induced by the excessive light absorption properties of certain skin pigmentations. The problem is currently inadequately addressed by using high intensity LEDs. This results in an increased safety risk due to the potential for burns especially in the neonatal, infant and pediatric populations. The new art obviates this problem by supplying greater amounts of light (and no waste heat) from the remote source. The system is also inherently immune to extraneous light interference, which reduces false alarms.

Because of the use of a laser light source, the typical difficult cases, i.e. poor perfusion, highly pigmented skin and specific diseases states are eliminated and pose no particular challenge to the new system.

The main instrument portion of this invention is composed of the transmitting lasers, receiving detectors (or electronics for the second configuration), and electronics package as described above). This portion is designed to allow the device to emulate the signals from the current art. This is advantageous since users switching to the present inventive method do not need to replace the main unit they now use. This would save expense in both purchased equipment and retraining areas.

While the foregoing is a detailed description of the preferred embodiment of the invention, there are many alternative embodiments of the invention that would occur to those skilled in the art and which are within the scope of the present invention. Accordingly, the present invention is to be determined by the following claims.

We claim:

1. An apparatus for transmitting laser light through a portion of a living body, comprising:

a first source of laser light having a first frequency;

a second source of laser light having a second frequency;

a first fiber optic conduit to conduct said laser light having said first and second frequencies from said first and second sources to a vicinity of the portion of the living body, said first conduit having a main portion to receive said laser light from said first and second sources and a distal portion to conduct said laser light from the main portion of the first conduit to the vicinity of the portion of the living body;

a detection system to receive first and second signals which correspond to said first and second frequencies of laser light after said laser light has transmitted through said portion of the living body, said detection system having a distal portion to receive said first and second signals and a main portion to conduct said first and second signals to a measurement system that interprets said first and second signals; and at least one coupler to removably connect said main portion to said distal portion of said first conduit at a location remote from said first and second sources and closer to the portion of the living body than it is to said first and second sources, and to removably connect said main portion to said distal portion of said detection system at a location remote from said measurement system and closer to the portion of the living body than it is to said measurement system, wherein said distal portion of said detection system converts said transmitted laser light to first and second electrical signals.

2. A method for transmitting laser light through a portion of a living body, comprising the steps of:

a) providing a first source of laser light having a first frequency;

b) providing a second source of laser light having a second frequency;

c) providing a first fiber optic conduit to conduct said laser light having said first and second frequencies from said first and second sources to the vicinity of the portion of the living body, said first conduit having a main portion to receive said laser light from said first and second sources and a distal portion to conduct said laser light from the main portion of the first conduit to the vicinity of the portion of the living body;

d) providing a detection system to receive first and second signals which correspond to said first and second signals frequencies of laser light after said laser light has transmitted through a portion of the living body, said detection system having a distal portion to receive said first and second signals and a main portion to conduct said first and second signals to a measurement system that interprets said first and second signals;

e) removably interconnecting said main portion with said distal portion of said first conduit at a location remote from said first and second sources and closer to said portion of the living body than it is to said first and second sources; and f) removably interconnecting said main portion with said distal portion of said detection system at a location remote from said measurement system and closer to the portion of the living body than it is to said measurement system, wherein step d) further includes converting said transmitted laser light to first and second electrical signals within said distal portion of the detection system.

3. An apparatus for use in a pulse oximetry system, said apparatus comprising:

(a) a first laser light source for emitting laser light having a first frequency;

(b) a second laser light source for emitting laser light having a second frequency;

(c) a detector means for receiving light information and converting the received light information to electrical signals; and (d) an optical system for receiving and transmitting laser light from said first and second light sources through a portion of a living body and for receiving and transmitting light which has passed through said portion of said living body to said detector means, said optical system comprising:

(i) a permanent section comprising:
a first fiber optic cable having a proximal end for receiving the laser light received from said first and second light sources;
a second fiber optic cable having a proximal end for transmitting said light information to said detector means; and
a connector means for connection with distal ends of said first and second fiber optic cables; and (ii) a disposable section for directing light through said portion of said living body and receiving light which has passed through said portion of said living body and comprising a probe including:
a third fiber optic cable having a proximal end for detachable connection to said connector means to receive and conduct the laser light transmitted by said first fiber optic cable to a vicinity of said portion of said living body to be transmitted through said portion of said living body;
a fourth fiber optic cable having a proximal end for detachable connection to said connection means to receive and conduct light which has transmitted through said portion of said living body to said second fiber optic cable; and a terminal element comprising a substrate and a first optical element for receiving light from a distal end of said third fiber optic cable to direct light onto and through said portion of said living body and a second optical element for receiving light which has passed through said portion of said living body and transmitting the light to a distal end of said fourth fiber optic cable; said first and second optical elements being mounted on said substrate, wherein when said first, second, third and fourth fiber optic cables are connected to said connection means, said connection means is located closer to said distal ends of said third and fourth fiber optic cables than to said proximal ends of said first and second fiber optic cables.

4. An optical system for use in a pulse oximetry system, said pulse oximetry system employing a first laser light source for emitting laser light having a first frequency, a second laser light source for emitting laser light having a second frequency and a detector means for receiving light information and converting the received light information to electrical signals, said optical system for receiving and transmitting laser light from said first and second light sources through a portion of a living body and for receiving and transmitting light which has passed through said portion of said living body to said detector means, said optical system comprising:

(a) a permanent section comprising:
a first fiber optic cable having a proximal end for receiving the laser light from said first and second light sources;
a second fiber optic cable having a proximal end for transmitting said light information to said detector means; and
a connector means for connection with distal ends of said first and second fiber optic cables; and (b) a disposable section for directing light through said portion of said living body and receiving light which has passed through said portion of said living body and comprising a probe including:
a third fiber optic cable having a proximal end for detachable connection to said connector means to receive and conduct the laser light transmitted by said first fiber optic cable to a vicinity of said portion of said living body to be transmitted through said portion of said living body;
a fourth fiber optic cable having a proximal end for detachable connection to said connection means to receive and conduct light which has transmitted through said portion of said living body to said second fiber optic cable; and
a terminal element comprising a substrate and a first optical element for receiving light from a distal end of said third fiber optic cable to direct light onto and through said portion of said living body and a second optical element for receiving light which has passed through said portion of said living body and transmitting the light to a distal end of said fourth fiber optic cable, said first and second optical elements being mounted on said substrate, wherein when said first, second, third and fourth fiber optic cables are connected to said connection means, said connection means is located closer to said distal ends of said third and fourth fiber optic cables than to said proximal ends of said first and second fiber optic cables.

* * * * *